(12) United States Patent
Alini et al.

(10) Patent No.: US 8,999,001 B2
(45) Date of Patent: Apr. 7, 2015

(54) BIOCOMPATIBLE IMPLANT

(75) Inventors: Mauro Alini, Davos Platz (CH); Sophie Verrier, Davos Platz (CH); David Olivier Eglin, Davos Dorf (CH)

(73) Assignee: AO Technology AG, Chur (CH)

( * ) Notice: Subject to any disclaimer, the term of this patent is extended or adjusted under 35 U.S.C. 154(b) by 78 days.

(21) Appl. No.: 12/988,976

(22) PCT Filed: Apr. 21, 2008

(86) PCT No.: PCT/CH2008/000181
§ 371 (c)(1),
(2), (4) Date: Oct. 21, 2010

(87) PCT Pub. No.: WO2009/129631
PCT Pub. Date: Oct. 29, 2009

(65) Prior Publication Data
US 2011/0040388 A1   Feb. 17, 2011

(51) Int. Cl.
*A61F 2/28*   (2006.01)
*A61L 27/36*   (2006.01)
*A61L 27/38*   (2006.01)
*A61L 27/46*   (2006.01)
*A61L 27/56*   (2006.01)
*A61L 27/58*   (2006.01)

(52) U.S. Cl.
CPC ........... *A61L 27/365* (2013.01); *A61L 27/3616* (2013.01); *A61L 27/38* (2013.01); *A61L 27/46* (2013.01); *A61L 27/56* (2013.01); *A61L 27/58* (2013.01); *A61L 2430/02* (2013.01)

(58) Field of Classification Search
USPC ........................................... 623/23.51, 23.61
See application file for complete search history.

(56) References Cited

U.S. PATENT DOCUMENTS

| | | | |
|---|---|---|---|
| 4,394,370 A | 7/1983 | Jefferies | |
| 4,472,840 A | 9/1984 | Jefferies | |
| 4,620,327 A | 11/1986 | Caplan et al. | |
| 4,623,553 A | 11/1986 | Ries et al. | |
| 5,481,601 A | 1/1996 | Nazif et al. | |
| 5,585,007 A | 12/1996 | Antanavich et al. | |
| 5,599,558 A | 2/1997 | Gordinier et al. | |
| 5,614,204 A | 3/1997 | Cochrum | |
| 5,684,061 A * | 11/1997 | Ohnishi et al. | ................ 523/114 |
| 6,322,785 B1 | 11/2001 | Landesberg et al. | |
| 6,398,072 B1 | 6/2002 | Nitta et al. | |
| 6,811,777 B2 | 11/2004 | Mishra | |
| 7,172,629 B2 | 2/2007 | McKay | |

(Continued)

FOREIGN PATENT DOCUMENTS

| EP | 1 239 894 A1 | 9/2002 |
|---|---|---|
| EP | 1 508 311 A2 | 2/2005 |

(Continued)

OTHER PUBLICATIONS

International Search Report for PCT/CH2008/000181 dated Feb. 6, 2009.

(Continued)

*Primary Examiner* — Randy Shay
(74) *Attorney, Agent, or Firm* — Sughrue Mion, PLLC (57) ABSTRACT

A biocompatible implant for bone repair comprising a flexible membrane fitted around a bone defect and a platelet-rich plasma gel composition contained within the void space created by the membrane, its application and kit of parts thereof are described.

19 Claims, 5 Drawing Sheets

(56) References Cited

U.S. PATENT DOCUMENTS

2006/0241776 A1* 10/2006 Brown et al. .............. 623/20.16
2007/0282247 A1* 12/2007 Desai et al. .................... 604/19

FOREIGN PATENT DOCUMENTS

EP          1 920 788 A1    5/2008
WO          01/45760 A1     6/2001

OTHER PUBLICATIONS

Ferenc Dori et al., "Effect of Platelet-Rich Plasma on the Healing of Intrabony Defects Treated with Beta Tricalcium Phosphate and Expanded Polytetrafluoroethylene Membranes", Apr. 1, 2008, pp. 660-669, vol. 79, No. 4.

Jeroen P.M. Fennis et al., Reconstruction of the Mandible with a Poly (D, L-lactide) Scaffold, Autogenous Corticocancellous Bone Graft, and Autogenous Platelet-Rich Plasma: an Animal Experiment, Tissue Engineering, 2005, pp. 1045-1053, vol. 11, No. 7/8.

* cited by examiner

HAP µg/gel          µg HAP   2   6   10

BIOCOMPATIBLE IMPLANT

FIELD OF THE INVENTION

The present invention relates to a biocompatible implant for bone repair, in particular to a biocompatible implant comprising a flexible membrane fitted around a bone defect and a platelet-rich plasma gel composition contained within the void space created by the membrane, its application and kit of parts thereof.

BACKGROUND

Bone tissue has a remarkable ability to regenerate and thereby repair injuries and other defects. Such repair relies on an equilibrium between an anabolic (osteogenic) and a catabolic (bone resorption) process, i.e. an interplay between bone-forming cells, known as osteoblasts and bone-resorbing cells, known as osteoclasts, whereby bone is continuously being destroyed (resorbed) and rebuilt. Thus, typically under conditions where enhanced bone formation is needed, for example when bone tissue sustains damage such as a fracture, osteoblasts precursor cells proliferate and differentiate toward mature osteoblasts to regenerate bone. However, there are many circumstances, wherein osteoblasts cannot be activated effectively, such as in the case of complex bone fracture or damage, caused by e.g. severe injury, deformity, illness or during a surgical procedure, possibly in combination with osteomyelitis, or in the case of a disturbance in the fine-tuned balance between bone resorption and bone formation as a direct result of a number of diseases.

Treatment of such bone defects have typically been based on bone grafts. Autograft techniques have been known for over 100 years and include the use of cortical and cancellous bone as grafting material. While the use of autografts is preferred due to their low risk of disease transmission, it also presents several serious drawbacks including the limited amount of potential donor material available, the requirement of an additional surgical procedure, as well as size and shape limitations of the bone. Allografts on the other hand may have the benefits of avoiding two-site surgery on the patient, but they have increased risks of disease transmission and immunogenic implant rejection. Thus over the past decades research has focused on obtaining bone graft substitutes that could be used in place of the transplanted bone to stimulate bone healing and provide a strong and biologically compatible framework for new bone to grow into.

These alternatives include for example compositions based on demineralized bone matrix (DBM) (e.g. U.S. Pat. No. 5,481,601), collagen, various calcium phosphates, such as beta-tricalcium phosphate $(Ca_3(PO_4)_2)$ (beta-TCP), alpha-tricalcium phosphate (alpha-TCP) and hydroxyapatite (HA) (e.g. U.S. Pat. No. 4,623,553), and composites thereof, i.e. for example in combination with further osteoinductive materials, such as specific bone growth and differentiation factors, bone morphogenetic proteins (e.g. U.S. Pat. Nos. 7,172,629; 4,394,370; 4,472,840; 4,620,327), bone marrow cells (BMC), and more recently compositions based on platelet-rich plasma (PRP).

PRP is an enriched platelet-containing mixture containing 95% platelets with 4% red blood cells and 1% white blood cells. It is isolated from whole blood and resuspended in a small volume of plasma. Upon combination with activating agents such as thrombin or calcium chloride, the platelets are activated to release their contents such as cytokines and other growth factors. PRP has been used in medicine, primarily in bone grafting and dental implant applications. For example, U.S. Pat. No. 6,322,785 discloses an autologous, thrombin-free platelet gel that includes PRP and collagen (for activation) for craniofacial and joint reconstruction, dental implants as well as bone defects and fractures. In vitro preparation, gelling and subsequent insertion into a mandibular void is described. EP 1 508 311 describes the use of a tube consisting of hydroxyapatite ceramics and optionally having PRP introduced therein for fixing an implant in an alveolar bone or gnathic bone. EP 1 239 894 B1 discloses a bone generating product comprising a coagulated matrix of PRP with thromboplastin in the presence of at least a phospholipid and an effective amount of a calcium containing compound dispersed in the matrix for inducing the formation of bone.

Applications in other areas of medicine include for example PRP as part of a composition for wound healing (U.S. Pat. No. 5,599,558) and tissue repair (U.S. Pat. No. 6,811,777), for use as a tissue sealant (U.S. Pat. No. 5,585,007) or in combination with a biopolymer to temporarily block arteries and veins (U.S. Pat. No. 5,614,204).

To date the use of PRP in bone repair has been designed for treating smaller bone defects such as acquired and congenital craniofacial and other skeletal or dental anomalies (see e.g., Glowacki et al., Lancet 1: 959 (1981)); performing dental and periodontal reconstructions where lost bone replacement or bone augmentation is required such as in a jaw bone; and supplementing alveolar bone loss resulting from periodontal disease to delay or prevent tooth loss (see e.g. Sigurdsson et al., J Periodontol, 66: 511 (1995)). However, such repair appears to be quite different from the induction of bone formation required to fill non-union fractures, segmental gaps or bone voids caused, for example by injury or illness, such as removal of a bone tumor or cyst. These cases require bone grafting or induction of new bone growth employing a different type of matrix or scaffolding to serve as a bone growth substitute.

For such uses, compositions have been developed in form of a non-flowable mass, for example as sheets, puttys or in combination with biopolymers and/or have been crosslinked with e.g. glutaraldehyde, formaldehyde or other chemical crosslinking or subjected to gelling prior to application to a bone defect to provide a preformed scaffold and thereby reducing their flowability and ensuring their retention at the site of bone defect. However, this requires lengthy pre-treatment of the compositions and additions of foreign substances which may have adverse effects in vivo.

Clearly, no osteogenic composition has yet been found to be optimal in generalized usage, and clinical results vary widely even with seemingly well defined compositions. There remains a need for improved osteogenic implant materials that are consistently strongly osteoinductive and osteoconductive, and do not cause any adverse effects in vivo, that are easily accessible and allow ease of handling in surgical procedures, that provide strength and stability for new bone formation during the early stages of bone development, and that are applicable to all sizes of bone defects (ranging from small defects to large gaps). Preferably such compositions are essentially completely incorporated and remodelled into bone by the end of the osteogenic process, thus without need of further surgical procedures. The present invention is addressed to these needs.

Applicants have discovered that the above disadvantages can be overcome by using a biocompatible implant system comprising a PRP gel composition, optionally supplemented with autologous osteogenic factors, nanoparticulate minerals, etc., to induce and promote bone growth within the bone defect, in combination with a flexible, biocompatible membrane to retain the PRP gel composition within the bone defect.

The use of an injectable PRP gel composition in combination with a suitable membrane allows easy and rapid application without the need of extensive manipulation. In addition, the use of autologous material supplementing the PRP gel composition (and/or the membrane) reduces or eliminates adverse effects caused by foreign material. The injectable PRP gel composition may typically be scaffold free, however a skilled person will know that it may be supplemented with a biodegradable support structure depending on the nature and location of the bone defect, i.e. if additional stabilization is desired.

Thus the novel biocompatible implant shows great flexibility and allows the induction and promotion of bone growth within any kind and any size of bone defect.

SUMMARY OF THE INVENTION

Figure 1:
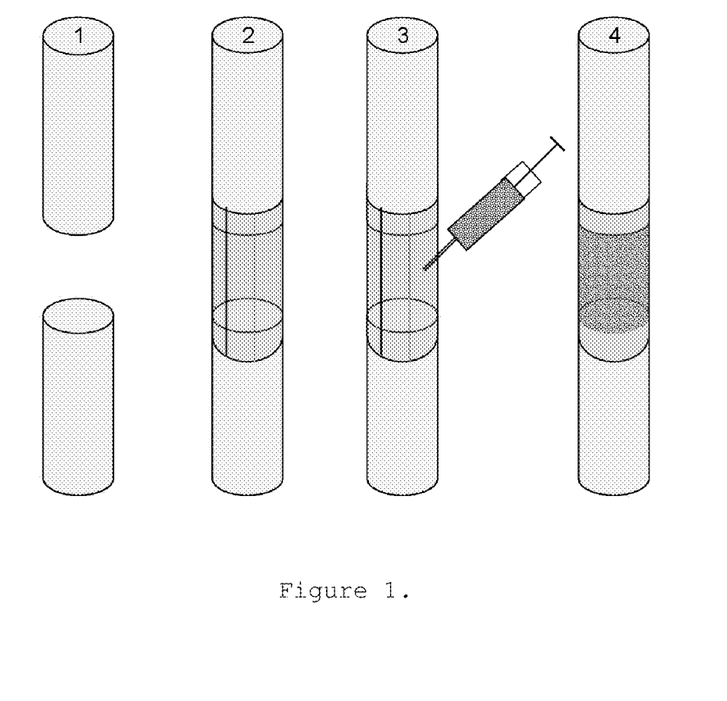
FIG. 1: Schematic view of a biocompatible implant for repair of bone defects according to the invention.

The present invention provides in a first aspect an improved osteogenic biocompatible implant for repair of a bone defect comprising a PRP gel composition and a flexible, biocompatible membrane, whereby said membrane is spanned around the bone defect site thereby creating a void space, into which the PRP gel composition is injected (FIG. 1).

In a specific embodiment the PRP gel composition comprises autologous cells of the same or different nature.

In a further specific embodiment the PRP gel composition is of autologous nature and is either prepared in situ prior to surgical procedure or else stored at −20° C. upon preparation until further use.

In yet a further specific embodiment the PRP gel composition comprises at least one nanoparticulate mineral selected from the group consisting of hydroxyapatite, corraline hydroxyapatite, hydroxyapatite carbonate, bioactive glass ceramic, bioactive ceramic, calcium phosphate ceramic, calcined bone, tricalcium phosphate, or like material, preferably hydroxyapatite.

In a further specific embodiment the PRP gel composition may comprise an activation agent, such as a calcium salt or thrombin.

In a further specific embodiment the PRP gel composition is either prepared in situ prior to its immediate use in a surgical procedure or else stored at −20° C. upon preparation until further use.

In a further specific embodiment the PRP gel composition may further be contained within a support structure.

Figure 2:
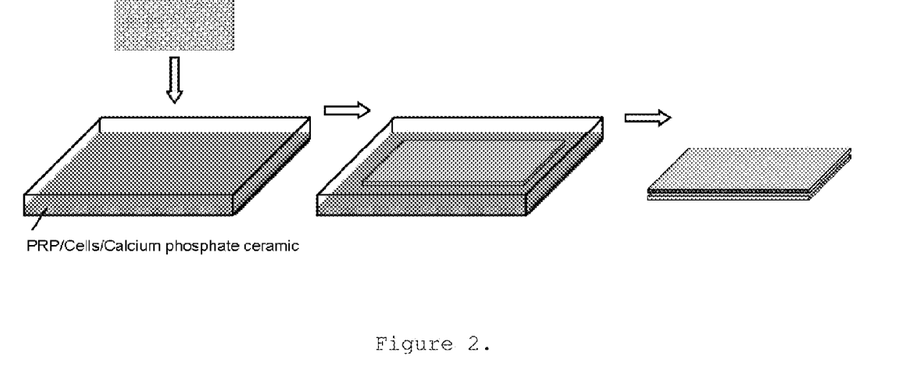
FIG. 2: Schematic of seeding of autologous EPC on membrane surface.
Figure 3:
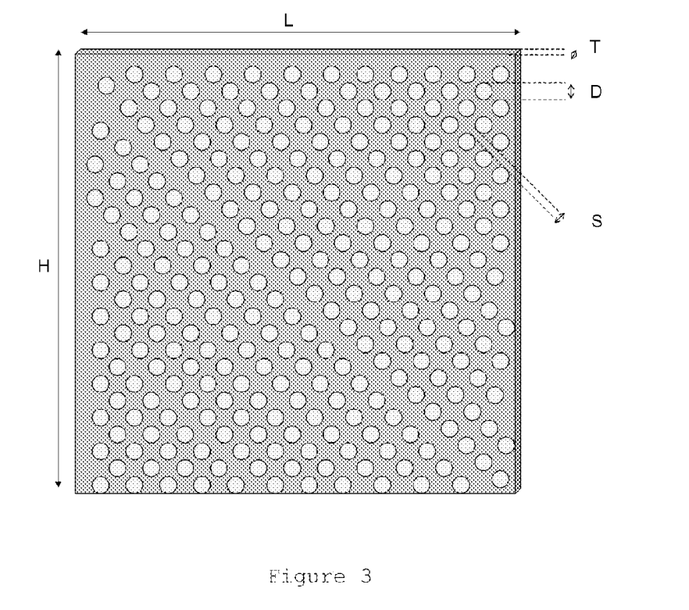
FIG. 3: Schematic view of a resorbable membrane (Length L, High H, Thickness T, Pores diameters D, shorter space in between two adjacent pores S).

In a further specific embodiment the membrane is seeded on one or both of its surfaces with cells, e.g. endothelial progenitor cells (EPC), MSC, and mixtures thereof and/or a PRP composition and/or nanoparticulate material, e.g. calcium phosphate particles prior to its use in enclosing or covering a bone defect (FIG. 2).

In a further specific embodiment the membrane is of sufficient flexibility to be spanned or fitted around a bone defect site, and of sufficient mechanical strength to retain a stable shape and maintain the PRP gel composition within the site of bone defect.

Preferably the membrane is biodegradable thus eliminating the need for removal by additional surgical procedures. Preferred materials include hydrolyzable polyesters such as polylactic acid and polyglycolic acid, and polyurethanes, including poly(ester-urethane), poly(ether-urethane), poly(urethane-urea), poly(ester-urethane-urea), and poly(ester-thiourethane) and copolymers, block copolymers and blends of the above materials.

The invention also provides methods for preparing such biocompatible implants and their use to induce bone growth and thus repair bone defects due to trauma, disease and any other defects, wherever osteogenesis is desired.

These and other objects, features and advantages of the present invention will be readily apparent from the following description.

DETAILED DESCRIPTION OF THE INVENTION

As used herein the term "bone defect", refers to any abnormality in the bone, including, but not limited to, a void, a cavity, a conformational discontinuity, a fracture or any structural change produced by injury, osteotomy, surgery, fractures, malformed healing, non-union fractures, skeletal deformations, aging, or disease.

As used herein the term "osteoinductive" refers to the ability of a material to induce the production of osteoblasts from precursor cells, in particular mesenchymal stem cells. An osteoinductive material may act directly as a growth factor which interacts with precursor cells to induce the osteoblast differentiation, or a material may act indirectly by inducing the production of osteoinductive growth factors. This induction also requires signaling, modulating, and transforming molecules. Osteoinduction may further comprise the differentiation of said osteoblasts into osteocytes, the mature cells of the bone.

As used herein the term "osteogenic" refers to the process of forming new bone. This formation requires signalling, modulating, and transforming molecules.

As used herein the term "osteoconductive" refers to materials which provide a favourable environment for ingrowth and orientation of osteogenic cells from surrounding tissues. Such materials are generally porous materials, i.e., providing latticework structures similar to cancellous bone.

As used herein the term "autologous" refers to cells, tissues or proteins that are reimplanted in the same individual as they were obtained from.

As used herein the term "angiogenic" refers to the formation of new blood vessels.

As used herein the term "biocompatible" refers to materials which, when used according to the present invention, show low toxicity, acceptable foreign body reactions in the living body, and affinity with living tissues.

As used herein, the term "resorbable" refers to the ability of a material to be resorbed in vivo. "Full" means that no significant extracellular fragments remain. The term "biodegradable" typically refers to a resorption of the original implant materials taking place through the action of body fluids, enzymes or cells. The term "bioerodible" typically refers to a resorption process by bulk or surface degradation. In vivo resorption may involve a combination of various processes.

As used herein, the term "subject" refers to a mammal, such as an animal or a human.

In a first aspect, the invention relates to a biocompatible implant for repair of a bone defect (hereinafter also called biocompatible implant of the invention) comprising a flexible membrane comprising a biocompatible material having an inner and an outer surface fitted or spanned around said bone defect to create an enclosed void space; and a PRP gel composition contained within the void space created by the membrane.

One embodiment of a biocompatible implant of the invention is schematically illustrated in FIG. 1, whereby a bone defect such as a bone gap (1) is first wrapped by a membrane according to the invention in tubular form to create a void space (2), and subsequently a PRP composition according to the invention is injected through the membrane into the void space using a syringe (3), to give the final biocompatible implant of the invention (4).

In another embodiment, a biocompatible implant of the invention a bone defect such as a cavity is covered by a membrane according to the invention to create a void space, and subsequently a PRP composition according to the invention is injected through the membrane using a syringe, to give the final biocompatible implant of the invention.

Depending on the nature and location of the bone defect the PRP gel composition may be supplemented with a support structure as described hereinafter.

In a specific embodiment, the PRP to be delivered to the void is prepared from the plasma of the patient in need of bone repair and/or from a plasma histocompatible with the patient, preferably from the plasma of the patient in need of bone repair. This will not only eliminate complications due to incompatibility but also ensures ease of handling and no delays in the preparations for subsequent implantation of the membrane and PRP gel composition.

The term "PRP" as used herein may be interpreted in its ordinary sense and represents a concentration of platelets greater than the peripheral blood concentration suspended in a solution of plasma, with typical platelet concentrations ranging from 500,000 to 2,000,000 per cubic millimeter.

The PRP was obtained according to standard procedures known in the art (see for example Marx, R. E. et al., Oral Surg. Oral Med. Oral Pathol. Oral Radiol. Endod., Vol. 85, 638-646, (1998); U.S. Pat. No. 6,398,972) and described in the experimental section. Briefly, it is formed from the concentration of platelets from whole blood and may be obtained using autologous, allogenic or pooled sources of platelets and/or plasma, preferably autologous sources. The so obtained PRP was either used immediately after activation steps for in vivo application (or in vitro evaluation PRP activation efficiency) or stored at −20° C. until further utilization. Prior to its utilization, supplements may be added as described below. Activation of the PRP was achieved through standard procedures, such as the freeze/thawing cycle. For example, the PRP, which was stored at −20° C., was thawed by incubation in a 37° C. water bath for 30-60 min.

In a further embodiment the PRP is supplemented with autologous cells. A wide variety of different autologous cell types may be used, including EPC or other mesenchymal stem cells (MSC), (bone) marrow stromal cells ((B)MSC), smooth muscle cells, progenitor cells (e.g. from bone marrow, adipose, or peripheral blood), and others, preferably EPC, MSC, and mixtures thereof, such as MSC/endothelial cells, MSC/EPC. Thus, the invention also contemplates a biocompatible implant as described above, wherein said platelet-rich plasma gel composition further comprises autologous cells.

In a specific embodiment, the cells of choice are either one cell type or a mixture of at least two cell types in varying proportions, e.g. EPC:BMSC in varying amounts (100%:0%, 5%:95%, 10%:90%, 25%:75%, 50%:50%, 75%:25%, 0%:100%) are typically trypsinised and the chosen number of cells is collected and mixed together with the PRP. Total cell number may vary from 10,000 to 2,000,000 total cell number per samples of 300 µL final volume, more preferably from 100,000 to 1,000,000 total cell number per samples of 300 µL final volume. Those amounts are to be adapted accordingly for larger volume samples.

As indicated hereinabove, PRP represents a natural autologous mixture comprising concentrated growth factors in a concentration (which may differ from one subject to the other). Thus, in a further embodiment the PRP may be further supplemented if desired with one or more of the following (already present) substances in variable proportion (to e.g. enrich one or more specific growth factors): platelet derived growth factor AB (PDGF-AB), platelet derived growth factor AA (PDGF-AA), platelet derived growth factor BB (PDGF-BB), vascular endothelial growth factor (VEGF), transforming growth factor (TGF-p), epidermal growth factor (EGF), insulin-like growth factor (IGF), epithelial cells growth factor ECGF and fibroblastic growth factor (FGF).

In yet a further embodiment the PRP may also be optionally supplemented with angiogenic and/or osteogenic factors. Suitable angiogenic factors may include any substance useful in a procedure that promotes the growth of new vessels including small molecule drugs, active compounds, gene products and genetic therapy agents, as well as cytokines or provisional matrix proteins or both. More specifically it may include one or more of the following substances: biologically active carbohydrates, recombinant biopharmaceuticals, agents that are active in the regulation of vascular physiology, such as nitric oxide agents that effect the regulation of gene activity by modulating transcription, the turnover of cellular mRNA, or the efficiency with which specific mRNA is translated into its protein product, i.e., antisense pharmaceuticals. Other active compounds include hormones, receptor ligands, peptides (both synthetic and naturally occurring), peptidomimetic compounds, specific and non-specific protease inhibitors, prostaglandins, inhibitors of prostaglandin synthase and/or other enzymes involved in the regulation of prostaglandin synthesis, growth factors that affect the vasculature such as acidic and basic FGF, FGF, VEGF, angiogenin, TGF alpha, and TGF beta.

In yet a further embodiment the PRP is supplemented with at least one nanoparticulate material. Suitable minerals may include one or more of the following substances: calcium phosphates, such as beta-tricalcium phosphate $(Ca_3(PO_4)_2)$ (beta-TCP), alpha-tricalcium phosphate (alpha-TCP) and hydroxyapatite (HAP) such as for example described in WO 2007/045977 (which is incorporated herein by reference in its entirety), calcium silicate, calcium carbonate or bioactive glasses and ceramics, which are mainly composed but not always of $SiO_2$, $Na_2O$, $CaO$ and $P_2O_5$, preferably HAP, a bioactive glass or ceramic.

Thus, the invention also contemplates a biocompatible implant as described above wherein said platelet-rich plasma gel composition further comprises at least one nanoparticulate material as defined above (and optionally comprises autologous cells as defined above).

Preferably the particulate mineral has an average particle diameter of about 1 nm to about 5 µm, preferably 1 nm to 1 µm, more preferably 10 nm to about 0.5 µm.

Preferably the at least one nanoparticulate mineral constitutes about 0.01% to about 60%, preferably 0.01% to 10% by volume of the PRP gel composition.

PRP jellification is initiated by addition of at least one suitable activation or jellifying agent, which is for the purpose of the present invention defined as a compound that is able to activate the release of platelet growth factors and the conversion of fibrinogen into fibrin. Thus, in yet a further embodiment the PRP is supplemented with an activation agent. The activation agent can be a natural, a synthetic and/or an inorganic activation agent. Suitable activation agents are compatible with the other constituents for effecting jellification or clotting of the autologous PRP gel composition. Examples include, but are not limited to, a calcium salt (e.g. calcium chloride or calcium gluconate), thrombin (human or bovine), batroxobin, or other activators (for example collagen, ADP and serotonin, as described in U.S. Pat. No. 6,322,785). Preferred activation agents include thrombin and calcium chloride.

Thus, the invention also contemplates a biocompatible implant as described above wherein said platelet-rich plasma gel composition further comprises at least one activation or jellifying agent as defined above (and optionally comprises autologous cells and/or at least one nanoparticulate material as defined above).

Depending on the required gel properties (e.g. jellification time, stiffness of the gel), varying concentration of the considered jellifying agents may be added.

Preferably said agent does not comprise additional organic compounds and in particular not any ionophores in order to keep toxicity low.

The PRP gel composition may be activated in vivo or ex vivo.

In one embodiment the PRP gel composition is activated ex vivo. The ex vivo activation of platelets or PRP can be done chemically or physically including addition of bovine thrombin, sonication, or the addition of an ionophore.

In a more preferred embodiment the PRP gel composition is activated using repeated freeze-thaw cycles. Activation efficiency is comparable to other methods (e.g. sonication).

In a further embodiment the PRP gel composition has preferably a pH substantially equal to the physiological pH, for example a pH comprised between 6.5 and 8, preferably about 7-7.5, pH measured at 37° C. Typically there is no need for altering the pH during storage or when ready for use.

A person skilled in the art will know, that the amounts or volumes of a PRP gel composition to be used for application in bone repair, depend on the size of the bone defect to be repaired. Preferably, the total volume of the PRP gel composition varies from 1 $cm^3$ to 20 $cm^3$. In one embodiment the PRP gel composition is pre-incubated in a 37° C. cell culture incubator until jellification has occurred (between 1 min and 2 hours, preferably 30 min, depending of the gel volume) and is then placed in a bone defect, which is subsequently enclosed by fitting around it a bioartificial periosteum membrane according to the invention.

In another embodiment, a bioartificial periosteum membrane is wrapped around a bone defect to create a void space and the PRP gel composition is directly injected prior to full jellification into the bony void and contained therein by the bioartificial periosteum membrane and then jellification takes place within the bony void.

In yet another embodiment, the PRP gel composition is supplemented with or contained in a suitable, biocompatible support structure. The platelet-rich plasma gel composition is delivered either before or after the support structure is placed into said bone defect. Thus, in one embodiment the PRP gel composition is first delivered to a biocompatible support structure, which is subsequently placed into a bone defect, which defect is then enclosed by fitting a membrane according to the invention around it. Alternatively, a suitable, biocompatible support structure is first placed into a bone defect, the PRP composition is then delivered to said support structure prior to full jellification, and the defect is enclosed by fitting a membrane according to the invention around it. Delivery of the platelet-rich plasma gel composition is typically done by injection.

A skilled person designing the suitable support structure for the intended application, will know that depending on the nature and location of the bone defect to be repaired, a support structure of different characteristics, e.g. pore size, shape, interconnection, degradation time, etc., may be suitable.

In a specific embodiment the support structure is resorbable and/or biodegradable. Preferably, the support structure is prepared from resorbable and/or biodegradable polymers, ceramics or resorbable polymer-ceramic composites.

Examples of resorbable polymers include but are not limited to collagen, hyaluronic acid, cellulose, and the like. Others examples of degradable polymers include but are not limited to polylactic acid and polyglycolic acid, poly(3-hydroxybutanoate), poly(3-hydroxyvalerate), poly(4-hydroxybutanoate), poly(ε-caprolactone), poly(valerolactone), polyorthoesters, polyanhydrides, polyurethanes, polyacrylic, polyhydroxymethacrylate, polymethylmethacrylate, polyamide, and copolymers, block copolymers and blends of the above materials, more preferably polylactic acid and polyurethanes, most preferably polyurethanes (which includes poly(ester-urethane), poly(ether-urethane), poly(urethane-urea), poly(ester-urethane-urea) and poly(ester-thiourethane)). Examples of resorbable ceramics include but are not limited to hydroxyapatite, coralline hydroxyapatite, hydroxyapatite carbonate, bioactive glass ceramic, bioactive ceramic, calcium phosphate ceramic, calcined bone, tricalcium phosphate, or like material or a mixture of the aforementioned ceramics. Examples of resorbable polymer-ceramics composites include but are not limited to a blend or a composition of any of the above mentioned polymers and ceramics, most preferably polyurethane and hydroxyapatite composites.

A suitable support structure according to the invention will exhibit a resorption rate in vivo from 1 month to 3 years, preferably 2 months to 12 months. Such a resorption rate can be adjusted using methods known to those skilled in the art, such as altering the polymer molecular weight, the polymer chain orientation and crystallinity, physical structure, chemical composition, presence and extent of voids, additives, etc.

In another specific embodiment the support structure is porous, preferably having a porosity in the range of 30% to 99%, more preferably between 60% to 95%. Preferably, the pore sizes range from 5 to 2000 µm, more preferably from 50 µm to 1000 µm.

In yet another specific embodiment the support structure is shaped in the form of the bone defect or press-fitted into the bone defect. Thus in one embodiment, the support structure is in form of a sponge, foam, gel or network of fibers or the like.

In another specific embodiment, the implantable biocompatible material for use as a flexible membrane in the biocompatible implant described hereinabove should be non-toxic, non-inflammatory, non-immunogenic and devoid of other undesired reactions at the implantation site. Further it should have sufficient flexibility to be spanned around the bone defect, thus adapting to any size or shape of bone defect with no need for performing it into precise shapes either prior to implantation or during the surgical procedure itself.

As used herein the wording "fitted around", "wrapped around" or "spanned around" means covering or enclosing a defect such that a void space is created. Thus, in case of a bone gap, such a membrane is "fitted around" the gap in "essentially tubular form" (see for example FIG. 1), which term includes any form that is obtained upon wrapping the membrane around a bone gap thereby enclosing the gap between the bone ends and forming a void space. In case of a bone cavity, such as found e.g. in cranio-maxillo-facial applications, such a membrane is "fitted around" the cavity in form of a lining or covering thereby also enclosing the cavity and forming a void space.

Furthermore the implantable biocompatible material should have sufficient mechanical strength to maintain a stable three dimensional structure, thereby maintaining the PRP gel composition within the site of bone defect and thus eliminating any deformation, migration or flowing away of the PRP gel composition from the implant site before ossification is established. Furthermore it should preferably be designed to be resorbed upon such ossification with no need for removal by additional surgical procedures. Furthermore, it should provide at least on its inner surface an adequate support for endothelial cells to attach and spread throughout its interconnected porosity to allow new vascularization.

Suitable materials include preferably porous matrices to allow for circulation of biological molecules. The materials of choice may be made porous by any techniques known to those of ordinary skill in the art that will render the device capable of allowing cell and blood vessel through-growth into the void space established by the membrane spanning the bone defect. Such techniques include, but are not limited to: sintering carefully controlled sizes of beads; combining the materials of different degradation rates, such that one material is resorbed first (in vivo or ex vivo) and will leave a partially resorbed, porous structure; weaving or knitting fibers together to form a fabric-like material; using a foaming agent during processing to cause bubbles to form and leave pores as the material hardens; solvent/solution phase-separation; laser etching; ion beam etching; and particle leaching incorporating particulates such as salt or gelatin into the material structure and dissolving out the particles leaving porous voids.

A skilled person designing the resorbable membrane for intended application, will know how to choose the degree of porosity, to allow for e.g. migration of bone progenitor cells, attachment of osteogenic cells, and diffusion of nutrients, by-products and the like and vascularization to further support bone and tissue growth.

This range of porosity can be described by micro- and nanoporosity. Within the scope of this invention, microporosity is defined as having a pore diameter less than 1000 μm but greater than or equal to 5 μm, and nanoporosity is defined as having a pore diameter less than 5 μm, preferably between 100 nm and 5 μm.

Monoporosity or bimodal porosity with varied pore size range, i.e. a membrane that includes both nanopores and micropores, could either be used depending of the membrane desired properties: permeability, cells attachment and spreading, vascularization, etc. Furthermore porous matrices may also provide for release of an active ingredient, for example in a slow, sustained release over time at the implantation site and therefore further accelerate the rate of bone growth.

Thus in a further embodiment cells (preferably autologous cells), such as EPC, MSC and mixtures thereof, but also total bone marrow, osteoconductive materials, such as ceramics, e.g. calcium phosphate, hydroxyapatite and the like, and/or osteoinductive materials, such as growth factors, e.g. bone morphogenetic protein (BMP) and the like, and/or other biologically active compounds, such as drugs, fatty acids, antibiotics and the like, may also be incorporated into the matrices or seeded onto one or both surfaces (preferably the surface facing inwards towards the bone defect) to support and accelerate bone formation.

In preferred embodiments, total bone marrow and/or cells, such as EPC, MSC or a mixture thereof (for example EPC/MSC 10%:90% of total cell number) and/or a PRP gel composition of the invention and/or ceramic particulates, e.g. in an amount of 1% to 20%, preferably 1% to 10%, most preferably 5% weight/volume of ceramic particulates are seeded onto one, preferably the inner, or both surfaces of the membrane of the invention.

The materials to be used as membranes may be of natural or synthetic origin and are preferably biodegradable.

There are a number of synthetic biodegradable polymers that can serve as suitable membranes with sustained release characteristics. Descriptions of these polymers can be found for example in Lichun et al., Polymeric Delivery Vehicles for Bone Growth Factors in "Controlled Drug Delivery-Designing Technologies for the Future", Park and Mrsny eds., American Chemical Society, Washington, D.C. (2000), Gunatillake P. A. and Adhikari R., Europ. Cells and Materials, 5, 1-16, 2003; Holland T. A. and Mikos A. G., Adv. Biochem. Eng Biotechnol. 102, 161-85, 2006; Nair L. S. and Laurencin C. T., Adv Biochem Eng Biotechnol. 102, 47-90, 2006, which are incorporated herein by reference in their entirety.

Examples of these polymers include but are not limited to biodegradable and non-biodegradable polymers such as collagen, hyaluronic acid, cellulose, degradable polyesters such as polylactic acid and polyglycolic acid, poly(3-hydroxybutanoate), poly(3-hydroxyvalerate), poly(4-hydroxybutanoate), poly(ε-caprolactone), poly(valerolactone), polyorthoesters, polycarboxylates, polycarbonates, polyanhydrides, polyurethanes, polytetrafluoroethylenes, perfluorinated polymers such as fluorinated ethylene propylenes, polypropylenes, polyethylenes, polyethylene terapthalates, silicones, polysufones, polyacrylic, polyhydroxymethacrylate, polymethylmethacrylate, polyamide, and copolymers, block copolymers and blends of the above materials, preferably biodegradable polymers such as collagen, hyaluronic acid, hydrolyzable polyesters such as polylactic acid and polyglycolic acid, polyorthoesters, polycarboxylates, polycarbonates, polycaprolactones, polyanhydrides, polyurethanes (which includes poly(ester-urethane), poly(ether-urethane), poly(urethane-urea), poly(ester-urethane-urea), poly(ester-thiourethane), preferably hydrolyzable polyesters and polyurethanes, more preferably polylactic acid and polyurethanes, most preferably polyurethanes.

Polyurethanes are well known in the art for use as biodegradable, biocompatible materials as for example described in WO 2006/010278, which is incorporated herein by reference in its entirety. Polyurethanes can be used alone or in combination with other polymers to obtain the desired characteristics, such as suitable flexibility, mechanical strength (which includes thickness), porosity as well as degradation rate. Those characteristics can be adjusted by the skilled artisan by variation of the molecular weight of the polymer, formation of the membrane, and possibly ratio of one or more additional polymers. Polyurethanes properties can also be adjusted by varying the nature of reactants (e.g. polyols, chain extenders, isocyanates) and their respective concentrations.

Thus, preferred polyurethanes such as poly(ester-urethane) may contain for example poly($\epsilon$-caprolactone) segment, 1,6-hexamethylene diisocyanate and a chain extender such as isosorbide, poly(ethylene glycol) and the like, as described in WO 2006/010278 A1, which is included herein by reference in its entirety.

The preferred polyurethanes may be prepared according to standard procedures described (see for example WO 2006/010278; Gorna K. and Gogolewski S., J. Biomed. Mater. Res. 79A, 128-138, 2006, which are incorporated herein by reference in their entirety). For example, a diisocyanate such as hexamethylene-1,6-diisocyanate is reacted with a polyol (e.g. poly($\epsilon$-caprolactone)diol), and a chain extender (e.g. 1,4,3,6-dianhydro-D-sorbitol or isosorbide) in the presence of a catalyst (e.g. dibutyl tin dilaurate) in N,N-dimethylformamide at elevated temperatures, e.g. 80° C. for several hours, e.g. 24 hours. The polyurethane is precipitated out in ethanol and dried under vacuum at constant weight. Typical average molecular weight average is 250 000 g·mol$^{-1}$ as measured by size exclusion chromatography. The diisocyanate to polyol group and chain extender molar ratio is kept equal to 1:1, while the chain extender to polyol theoretical molar ratio can be varied from 0.1:1 and 10:1 and is preferably 0.5:1.

A skilled person designing the resorbable membrane for intended application, will know that depending on the nature of the bone defect to be repaired a different degradation time may be suitable. A polyurethane membrane suitable for a larger defect needs to show a longer degradation time in order to ensure sufficient retention of the gel composition until bone formation has sufficiently developed, while shorter degradation times may be adequate for smaller bone defects. Suitable degradation times may range from 4 to 36 months, preferably 12 to 36 months.

For use in the present invention the porosity of the polymer membranes of choice may range from 5 $\mu$m to 1000 $\mu$m, more preferably 50 $\mu$m to 500 $\mu$m. The thickness of the polymer membranes of choice for use in the present invention may range from 0.05 mm to 5 mm, preferably from 0.1 mm to 2 mm. A skilled person will know that the size of a suitable membrane depends on the size of the bone defect to be treated and preferably overlaps the bone defect to allow fixing the membrane to the intact bone. For example, membranes having a length of 5 cm to 35 cm, preferably 10 cm to 25 cm and a height of 5 cm to 35 cm, preferably 10 cm to 25 cm, are suitable.

In a further aspect the invention relates to the use of a biocompatible implant according to the invention in the repair of bone defects or a method for inducing bone growth in a subject.

For use in the present invention, the polymer of choice for use as the flexible membrane has to be configured into a desired configuration, which is a membrane of the desired size, including thickness and porosity as defined hereinabove. In one embodiment, the membrane may be constructed in such ways and provided with such mechanical properties that it can be configured, prior to implantation, into a desired configuration and that it will substantially retain the desired configuration of the established space (i.e. a gap, a cavity or the like) for a period of time necessary for substantially generating living bone within the space. In another embodiment, the membrane may be constructed such that it can be configured during implantation.

Upon implantation, the membrane provides a porous permeable boundary between the living tissues of the subject and the established void space created by the membrane surrounding the bone defect. The membrane therefore takes for example an essentially tubular form in case of a bone gap or a (flat) covering in case of a cavity (as defined hereinabove).

The membrane may delineate the entire boundary of the space, or else only a portion of the space, the remainder of the boundary being delineated by tissues of the subject. Preferably the membrane may delineate the entire boundary of the space. In a specific embodiment the ends of the membrane are overlapping with the bone ends, preferably by 0.01 to 5 cm, more preferably 0.5 cm to 3 cm.

Establishing and retaining the desired established space within the body of the subject may require the utilization of reinforcement means with the membrane. Thus these overlapping ends may be attached to the bone ends by suitable measures known in the art, such as staples, screws, sutures as well as struts, wires, or meshes, and the like.

The configuration (size and shape) of the space established by wrapping the membrane around the bone defect is essentially equivalent to the configuration of living bone desired for achieving full function of the bone again. Thus, preferably, the generation of living bone does not occur substantially outside the space established by the membrane wrapping around the bone defect.

As indicated hereinabove the period of time necessary for substantially retaining the established space may vary depending on the location of bone defect, the volume and dimensions of living bone to be generated, the nature of the PRP gel composition to be used (i.e. the amount of supplementation by autologous cells, osteogenic factors and the like and/or the presence of a support structure) as well as the constitution of the subject in need of bone repair. The mechanical characteristics required for substantially retaining the established space are of particular importance when degradable materials are used in the construction of the device or the reinforcement members. These degradable materials must not lose the capability of maintaining the desired established space prematurely.

Thus in one embodiment, at or soon after placement of the membrane onto or around the bone defect, the void space established is being filled with the PRP gel composition of the invention. The use of an injectable PRP gel composition according to the invention allows easy delivery to the void space by conventional means which includes using a syringe or a catheter. Upon injection of the PRP gel composition according to the invention into the void space, jellification is initiated if jellifying agents are present. With time, natural biological processes (cell differentiation and growth followed by matrix synthesis, vascularization) will lead to bone neo formation and resorption of the biocompatible implant of the invention. Thus, in one embodiment the present invention relates to a method for inducing bone growth in a subject, comprising (a) spanning a bone defect with a flexible membrane comprising a biocompatible material having an inner and an outer surface and optionally fixing the ends of the membrane to create a void space, and injecting a platelet-rich plasma gel composition into said void space, allowing bone growth to occur.

In another embodiment, a PRP gel composition supplemented by a support structure, may first be applied to a bone defect such as a bone gap (as shown in FIG. 1) or a cavity (not shown), and subsequently a membrane according to the invention is wrapped in tubular form around the gap or placed over the cavity for enclosure, to give the final biocompatible implant of the invention. In one particular embodiment, the PRP gel composition is first injected into a support structure, which is then placed into the bone defect. In another particular embodiment, a support structure of choice is first placed into a bone defect and the PRP gel composition is delivered after placement of the support structure into the bone defect.

Thus, in another embodiment the present invention relates to a method for inducing bone growth in a subject, the method comprising: (a) placing a biocompatible support structure into a bone defect, (b) delivering a PRP gel composition into said biocompatible support structure, and (c) spanning said bone defect with a flexible membrane to enclose said support structure and retain it within the bone defect, allowing bone growth to occur.

Alternatively, the present invention relates to a method for inducing bone growth in a subject, the method comprising (a) delivering a PRP gel composition into a biocompatible support structure, (b) placing said biocompatible support structure comprising the PRP gel composition into a bone defect, and (c) spanning said bone defect with a flexible membrane to enclose said support structure and retain it within the bone defect, allowing bone growth to occur.

In yet a further aspect the invention relates to a kit-of-parts for the preparation of a biocompatible implant according to the invention. In particular the kit-of-parts comprises one or more ready-to-use compartments for preparing the PRP gel composition in situ (which includes harvesting PRP from a subject in need of bone repair, purification of the obtained PRP, mixing the PRP with optional supplements), a further compartment containing a flexible, sterilized membrane, at least one further compartment with optional supplement(s).

Optionally the kit-of-parts also comprises a further compartment with a syringe and needle (e.g. 18 gauge) for injection of the PRP gel composition prepared in situ.

Thus in one particular embodiment the kit-of-parts comprises a first compartment with one or more containers (e.g. Monovettes® or other) for blood sampling(s) of a subject in need of bone repair, a second compartment with one or more sterile assay tubes (e.g. Falcon or other) for thrombocytes separation, a third compartment with one or more sterile assay tubes (e.g. Falcon or others) for performing the second preparation step of the PRP gel composition (i.e. platelet separation from plasma), a fourth compartment containing a flexible, sterilized membrane of suitable size (e.g. 20 cm by 15 cm size, to be cut into a specific size if desired prior to use according to the invention), a fifth compartment with a syringe and needle (e.g. 18 gauge) for injection of the PRP gel composition prepared in situ, at least one further compartment with optional supplements, such as bio-active ceramic particulates (e.g. HAP, CaP or else), an optional further compartment with a suitable support structure, and a last compartment for mixing of the PRP gel composition with the optional supplements (e.g. particulates, cells, etc).

While this invention has been particularly shown and described with references to preferred embodiments thereof, it will be understood by those skilled in the art that various changes in form and details may be made therein without departing from the scope of the invention encompassed by the appended claims.

EXAMPLES

Materials and Methods

Imaging: Images were made by contact radiography using a Faxitron X-ray cabinet (model 43855A) and Structurix AGFA films Cells: Endothelial cells were harvested from the eventual recipient, e.g. by removal of a saphenous vein and culture of the endothelial cells. Progenitor cells are preferably used and can be obtained from bone marrow biopsies or isolated from the circulating blood, and cultured in vitro. MSCs were from the recipient's bone marrow samples and expanded in vitro until the required cell number was reached (typically 2 to 4 weeks)

Culture Methods: The culture methods were standard culture techniques with special precautions for culturing of human cells with the intent of re-implantation.

PRP Preparation: Blood aspirates obtained from subjects in need of treatment were transferred from CPDA-cuvettes (provided in the kit) into 15 mL Falcon tubes (provided in the kit), and were centrifuged at 200 g for 30 min at RT. The resulting plasma supernatants were pooled, transferred into a new 15 mL Falcon tube, and centrifuged at 2,000 g for 5 min at RT to get a platelet pellet. PRP was produced therefrom by resuspending the resulting pellet in the remaining plasma supernatant ($1/10^{th}$ of the initial blood volume). PRP was either used immediately for in vitro evaluation of PRP activation efficiency or in vivo (upon optional addition of supplements) or stored at $-20°$ C. until utilization.

PRP Activation: PRP was activated through freeze/thawing cycle. The PRP was frozen at $-20°$ C. for a minimum of 30 min, or until utilization. Then samples were thawed by incubation in a 37° C. water bath for 30-60 min. Different percentages of thrombin (10 to 30% vol/vol of 50 U/mL stock solution) were added to the PRP to achieve the required gel texture and delay of jellification.

Figure 4:
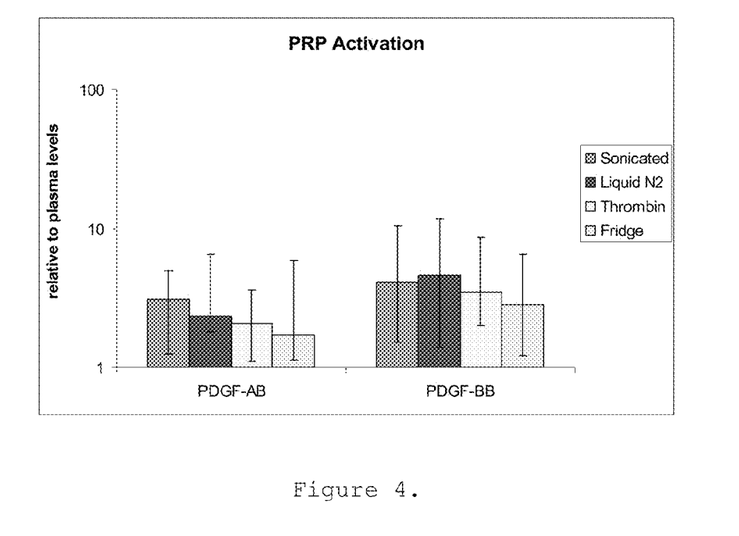
FIG. 4: Growth factor release upon PRP activation method.

Protein Release Upon Activation. To estimate platelet activation efficiency of the method described above, the release of PDGF-AB, -BB, and VEGF was determined by ELISA assay. The samples were centrifuged at 18,000 g for 2 min to pellet debris. The resulting liquid supernatant was diluted 1:50 in PBS containing 0.1% BSA and human VEGF, PDGF-AB and -BB protein content was measured using a DuoSet ELISA Development System by R&D Systems (PDGF-AB: DY222, PDGF-BB: DY220, VEGF: DY293B) on a Perkin Elmer Bio Assay Reader HTS 7000.FIG. 4 shows that the different activation modes present the same growth factor's release efficiency.

Example 1

Cell Encapsulation in PRP Gel

Total cell number varied from 100,000 to 2,000,000 total cell number per samples. PRP jellification was initiated by thrombin addition. Varying percentage (vol/vol) of a 50 U/mL thrombin solution was added (from 10 to 30%) in order to achieve the required gel properties (e.g. jellification time, stiffness of the gel).

For in vitro assays, 300 μL of the preparation were transferred into a mould (LabTeck chamber slides, Nunc) and placed at 37° C. for 20 minutes until jellification is completed. Samples were then removed from the mould, placed in 24 wells culture plate containing cell culture medium and further incubated in a 37° C. 5% $CO_2$ humidified atmosphere incubator.

Figure 5:
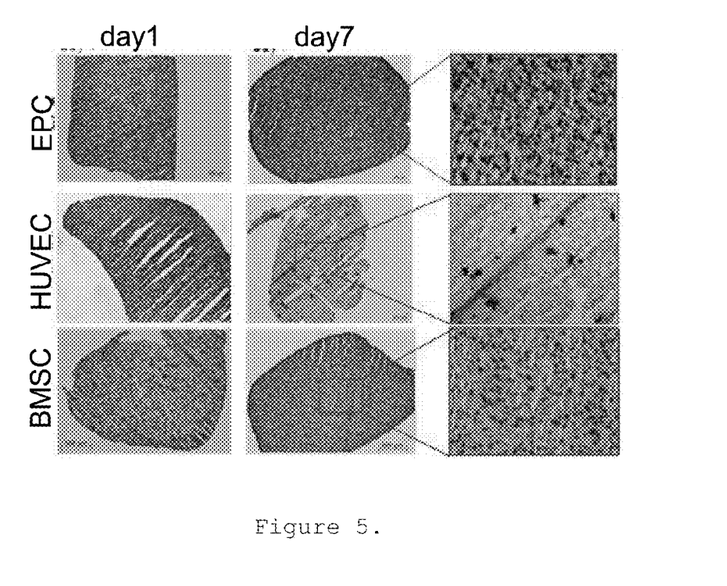
FIG. 5: Viability of EPC, MSC (from bone marrow origin: BMSC) and human umbilical vein endothelial cells (HUVEC) after 1 day and 7 days in culture in PRP gel.

It was observed that EPC and BMSC were still alive after 7 days in PRP gel in culture, while HUVEC showed a lower viability rate (FIG. 5).

Example 2

Hydroxyapatite Nano-Particles (HAP) Encapsulation in PRP Gel

PRP was prepared and activated as described hereinabove. Variable amounts of inorganic nano-particles were mixed with the PRP/cells preparation. Different PRP/Thrombin proportions were tested to determine optimal conditions of gel formation as well as gel texture: 10, 15, 20, 25 and 30% (vol/vol) thrombin (50 U/mL stock solution) were mixed to PRP (total volume of 300 μL in this experiment). Percentage of thrombin between 15 and 20% was most appropriate.

Figure 6:
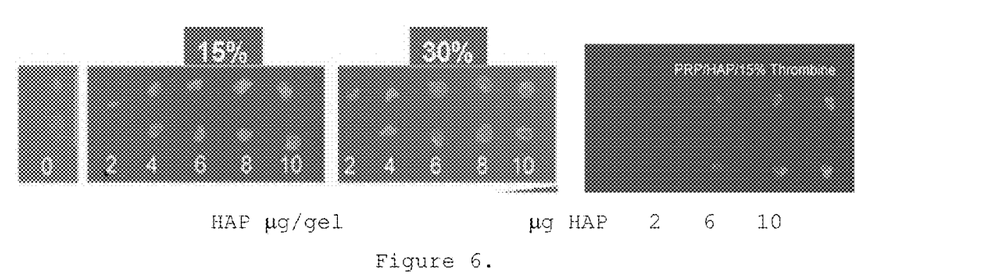
FIG. 6: Faxitron X-ray images of PRP gels with varying concentration of hydroxyapatite particles (HAP) and thrombin.

Different amounts of HAP were added to the PRP gel, and different thrombin percentages were tested. Faxitron X-ray images presented in FIG. 6 show the presence/repartition of HAP within the gel structure. Homogenous repartition of the HAP particulates could be achieved in all cases. The gel texture obtained using 15% thrombin was suitable of easy samples manipulation.

Example 3

Cell Encapsulation in PRP Gel HAP

Figure 7:
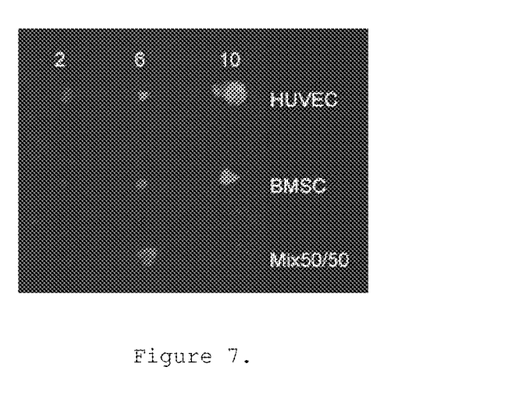
FIG. 7: Faxitron images of PRP/HAP gels (2, 6, or 10 µg/gel=6, 20, 33 µg/mL) containing either HUVEC, BMSC or a 50/50% mix of the 2 cell types.

PRP/HAP gel was prepared as described hereinabove, using 15% thrombin and either 2, 6 or 10 mg/gel (=6, 20, 33 mg/mL) HAP nanoparticles. Cells were trypsinised and the chosen number of cells was collected and mixed together with the PRP/HAP. Cell types were either mixed to PRP/HAP singly, i.e. one cell type only, or together with another cell type, i.e. a mixture of two or more cell types (e.g. MSC/endothelial cells, MSC/EPC). In the latter case, different proportions of the different cell types were used. Total cell number varied from 100,000 to 2,000,000 total cell number per samples. PRP jellification was initiated upon thrombin addition. Different percentages (vol/vol) of a 50 U/mL thrombin solution was added (from 10 to 30%). FIG. 7 shows Faxitron images of PRP/HAP gels (2, 6, or 10 mg/gel=6, 20, 33 mg/mL) containing either HUVEC, BMSC or a 50/50% mix of both cell types HUVEC and BMSC, whereby, 15% thrombin was added to the preparation. FIG. 7 indicates that even in presence of cells, it is possible to reach an acceptable homogeneity of nanoparticulates repartition within the gel.

Figure 8:
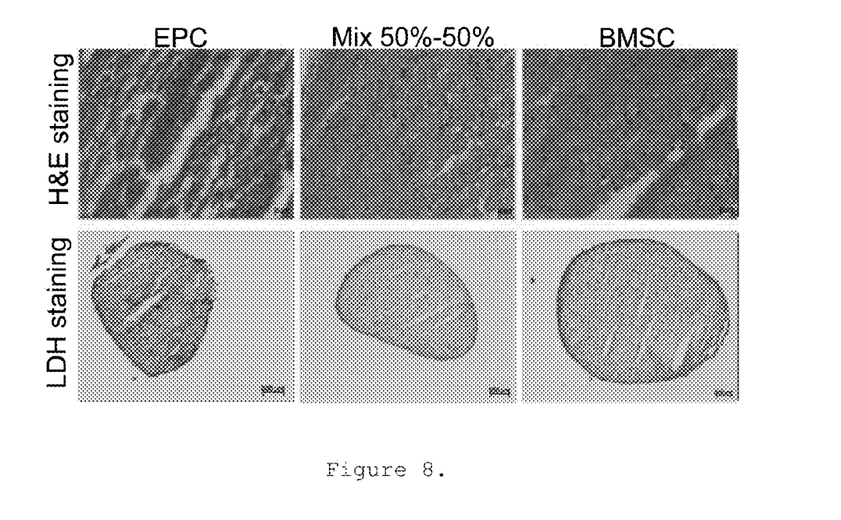
FIG. 8. Cell distribution and viability of EPC, BMSC or EPC/BMSC within a PRP/HAP by Haematoxylin Eosin staining and LDH activity.

Distribution and viability of either EPC, BMSC or a 50/50% mix of both cell types EPC and BMSC within a PRP/HAP gel was also tested respectively by Haematoxylin Eosin staining and LDH activity (see FIG. 8). A homogeneous cell distribution within the gel was obtained in all cases, and LDH activity staining shows that both cell types either alone or mixed were still alive even after 6 days in culture (FIG. 8).

Example 4

Porous Polyurethane Membrane Preparation

Figure 9:
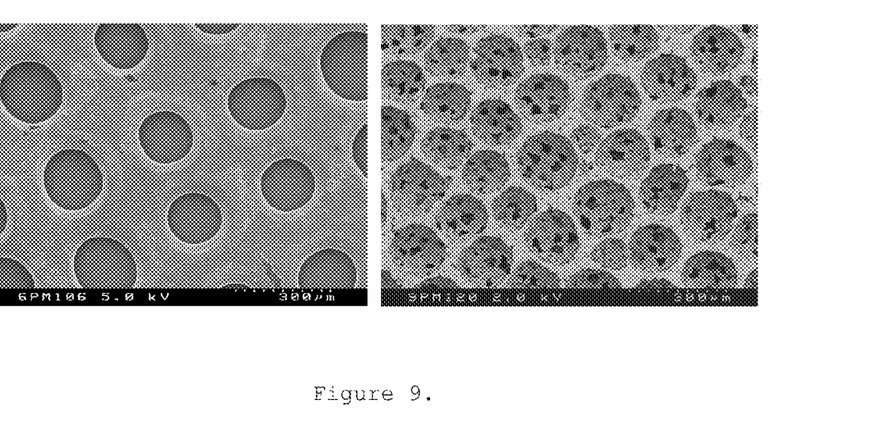
FIG. 9: SEM micrographs of laser-sintered polyurethane film (left); and poly(L/DL-lactide) (right) membrane prepared by an evaporation method.

A bioresorbable polyurethane membrane (D 100 μm, S 50 μm, T 0.05 mm, L 15 cm, H 20 cm) was prepared from a polyurethane with composition 1,6-hexamethylene diisocyanate, poly(ε-caprolactone) diol (MW 530 g/mol), isosorbide (molar ratio chain extender to polyol=0.5:1). 10 g of polyurethane (MW 250,000 g/mol) were dissolved in 200 ml of N,N-dimethylformamide and poured in a 20×35 cm tray. After slow evaporation of the solvent at room temperature for 5 days, a transparent film (50 microns thick) was obtained, washed with ethanol and further dried at 40° C. for 24 hours under vacuum. Micropores of 100 μm size were created subsequently in the film by using a 30 W $CO_2$ air-cooled computer controlled laser-cutter (FB400 series CadCam Technology Ltd, Nottingham, UK; resolution of laser beam: 25 μm). Directional control over the laser, raster/vector speed and output power was achieved by means of the proprietary software (ApS-Ethos). (FIG. 9).

Example 5

Porous Poly(L/DL-lactide) Membrane Preparation

Poly(L/DL-lactide) 80/20 wt % (Mn 300 000 g/mol) was purchased from PURAC. 5.15 g of poly(L/DL-lactide) 80/20 were dissolved in 266 ml of tetrahydrofuran. 27 ml of acetone and 4 ml of water were then added slowly to obtain a transparent homogeneous solution. Finally, 4 ml of a solution containing 39 g of citric acid dissolved in 50 ml of dimethylsulfoxide, was added dropwise. 226 ml of the solution was poured in a large glass tray (20×35 cm) and covered with a porous polyethylene sheet to control the solvent evaporation. The slow evaporation of the solution was performed at room temperature 23-25° C., with humidity in between 45% to 55% for 6 days. The obtained micro and nanoporous membrane (D 2-40 μm, S 200-20 μm, T 0.3 mm, L 15 cm, H 20 cm) was lifted from the plate with ethanol and dried at 40° C. for 24 hours (FIG. 9).

The invention claimed is:
1. A biocompatible implant for repair of a bone defect which comprises:
   (a) a flexible membrane comprising a biocompatible material having an inner and an outer surface capable of being fitted around said bone defect to create an enclosed void space, said membrane being seeded with autologous cells on one or both surfaces; and
   (b) a platelet-rich plasma gel composition capable of being injected through the membrane using a syringe within said void space created by the membrane and into contact with the inner surface of the membrane,
   wherein said platelet-rich plasma gel composition further comprises autologous cells of one type or a mixture of at least two types, and
   wherein when injected, the platelet-rich plasma gel composition is in contact with the inner surface of the flexible membrane,
   wherein said platelet-rich plasma gel composition further comprises a nanoparticulate mineral selected from the group consisting of hydroxyapatite, coralline hydroxyapatite, hydroxyapatite carbonate, bioactive glasses and ceramic, calcium phosphate ceramic, calcined bone, tricalcium phosphate,
   wherein the nanoparticulate mineral has an average particle diameter of 1 nm to 5 μm, and
   wherein the nanoparticulate mineral constitutes 0.01% to 60% by volume of the platelet-rich plasma gel composition.

2. The biocompatible implant of claim 1 wherein the total amount of said autologous cells ranges from 300,000 to 6,000,000 cells per mL of the platelet-rich plasma gel composition.

3. The biocompatible implant according to claim 1 wherein said platelet-rich plasma gel composition further comprises an activation agent, selected from the group consisting of calcium salt, thrombin, batroxobin, collagen, ADP and serotonin.

4. The biocompatible implant according to claim 3 wherein the activation agent constitutes 5 to 50% by volume of the platelet-rich plasma gel composition.

5. The biocompatible implant of claim 1, wherein the implant further comprises a support structure which contains the platelet-rich plasma gel composition after implantation.

6. The biocompatible implant of claim 5, wherein the platelet-rich plasma composition is injectable either before or after the support structure is placed into said bone defect.

7. The biocompatible implant of claim 5, wherein the support structure is porous.

8. The biocompatible implant of claim 5, wherein the support structure is resorbable and/or biodegradable.

9. The biocompatible implant of claim 5, wherein the support structure is in form of a sponge, foam, gel or network of fibers.

10. The biocompatible implant according to claim 1 wherein said biocompatible material is biodegradable.

11. The biocompatible implant according to claim 1 wherein said biocompatible material has a degradation rate ranging from 4 to 36 months.

12. The biocompatible implant according to claim 1 wherein said biocompatible material is a polymer selected from the group consisting of, hyaluronic acid, cellulose, degradable polyesters such as polylactic acid and polyglycolic acid, poly(3-hydroxybutanoate), poly(3-hydroxyvalerate), poly(4-hydroxybutanoate); poly(s-caprolactone), poly(valerolactone), polyorthoesters, polycarboxylates, polycarbonates, polyanhydrides, polyurethanes, polytetrafluoroethylenes, perfluorinated polymers such as fluorinated ethylene propylenes; polypropylenes, polyethylenes, polyethylene terapthalates, silicones, polysulfones, polyacrylic, polyhydroxymethacrylate, polymethylmethacrylate, polyamide, and copolymers, block copolymers and blends thereof.

13. The biocompatible implant according to claim 1 wherein said membrane is seeded on one or both surfaces with one or more materials selected from total bone marrow, cells, platelet-rich plasma gel composition, and ceramic particulates.

14. The biocompatible implant according to claim 1 wherein said membrane has a microporosity of 5 μm to 1000 μm.

15. The biocompatible implant according to claim 14 wherein said membrane has a nanoporosity between 100 nm to 5 μm.

16. The biocompatible implant according to claim 1 wherein said membrane has a thickness of 0.05 mm to 5 mm, a length of 10 cm to 25 cm, a height of 10 cm to 25 cm.

17. The biocompatible implant according to claim 1, wherein the implant is structured for inducing bone growth and implant neo-vascularization in a subject.

18. The biocompatible implant according to claim 1 wherein said nanoparticulate mineral is hydroxyapatite.

19. A biocompatible implant for repair of a bone defect comprising in combination:
 (a) a flexible membrane comprising a biocompatible material having an inner and an outer surface shaped and sized for fitting around said bone defect to create an enclosed void space, said membrane being seeded with autologous cells on one or both surfaces; and
 (b) a platelet-rich plasma gel composition injectable via a syringe through the membrane, into said void space created by the membrane and into contact with the inner surface of the membrane,
 wherein said platelet-rich plasma gel composition further comprises autologous cells of one type or a mixture of at least two types,
 wherein when injected, the platelet-rich plasma gel composition is in contact with the inner surface of the flexible membrane,
 wherein said platelet-rich plasma gel composition further comprises a nanoparticulate mineral selected from the group consisting of hydroxyapatite, coralline hydroxyapatite, hydroxyapatite carbonate, bioactive glasses and ceramic, calcium phosphate ceramic, calcined bone, tricalcium phosphate,
 wherein the nanoparticulate mineral has an average particle diameter of 1 nm to 5 μm, and
 wherein the nanoparticulate mineral constitutes 0.01% to 60% by volume of the platelet-rich plasma gel composition.

* * * * *